(12) United States Patent
Imbimbo et al.

(10) Patent No.: US 8,835,494 B2
(45) Date of Patent: Sep. 16, 2014

(54) DERIVATIVES OF 1-(2-HALO-BIPHENYL-4-YL)-ALKANECARBOXYLIC FOR THE TREATMENT OF NEURODEGENERATIVE DISEASES

(71) Applicant: Chiesi Farmaceutici S.p.A, Parma (IT)

(72) Inventors: Bruno Pietro Imbimbo, Parma (IT); Luca Raveglia, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 13/855,915

(22) Filed: Apr. 3, 2013

(65) Prior Publication Data

US 2013/0267592 A1 Oct. 10, 2013

(51) Int. Cl.
*A61K 31/215* (2006.01)
*C07C 69/76* (2006.01)

(52) U.S. Cl.
USPC ............ 514/531; 514/546; 560/102; 560/251

(58) Field of Classification Search
USPC .......................... 514/531, 546; 560/102, 251
See application file for complete search history.

(56) References Cited

U.S. PATENT DOCUMENTS 7,799,782 B2 * 9/2010 Munson et al. ............ 514/234.5

FOREIGN PATENT DOCUMENTS

WO    2004/074232    9/2004
WO    2006/016219    2/2006

OTHER PUBLICATIONS

European Search Report in Application No. 12163074.3 issued Sep. 11, 2012.

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

Pro-drugs of 1-(2-halo-biphenyl-4-yl)alkanecarboxylic acids are useful for preventing and/or treating neurodegenerative diseases, improving cognitive function and treating cognitive impairment.

19 Claims, No Drawings

DERIVATIVES OF 1-(2-HALO-BIPHENYL-4-YL)-ALKANECARBOXYLIC FOR THE TREATMENT OF NEURODEGENERATIVE DISEASES

CROSS REFERENCES TO RELATED APPLICATIONS

This application and claims priority to European Patent Application No. 12163074.3, filed on Apr. 4, 2012, which is incorporated herein by reference in its entirety.

BACKGROUND OF THE INVENTION

1. Field of the Invention

The present invention relates to pharmaceutical compounds which are useful for the prevention and/or treatment of neurodegenerative diseases or the treatment of cognitive function impairment. In particular, the present invention concerns pro-drugs of 1-(2-halo-biphenyl-4-yl)alkanecarboxylic acids. The present invention also relates to methods for the prevention and/or treatment of neurodegenerative diseases or the treatment of cognitive function impairment by administering such a compound.

2. Discussion of the Background

Neurodegenerative disorders such as Alzheimer's disease are characterized from a histopathologic point of view by a diffuse presence of extracellular and perivascular neuritic plaques and intracellular neurofibrillary tangles in the cerebral parenchyma of the patients. Neuritic plaques are mainly composed of aggregates of a protein with 39-43 amino acid residues known as β-amyloid (βA) and, depending on the numbers of amino acids, they are better known as $A\beta_{39}$, $A\beta_{40}$, $A\beta_{42}$ and $A\beta_{43}$.

In addition to these histopathologic lesions, there is lack of some neurotransmitters, particularly acetylcholine, serotonin, noradrenalin, dopamine, glutamate and substance P. The pharmacological approaches aimed at increasing acetylcholine cerebral levels, mainly through the administration of acetylcholine-esterase inhibitors, attained poor results from the clinical standpoint, or anyhow results which cannot significantly prevent the progress of the disease. For this reason, in recent years interest has been focused on the mechanisms of formation of the main pathologic lesions in the brain of the patients, namely both neuritic plaques and neurofibrillary tangles, and more effective therapeutic approaches have been looked for.

In this respect, compounds have been reported which can reduce the production of the most neurotoxic isoform of β-amyloid, namely the form containing 42 amino acids ($A\beta_{42}$), through their interaction with a macromolecular/multiprotein enzymatic complex with aspartyl-protease activity, known as γ-secretase.

For instance, WO 2004/074232 discloses derivatives of 1-(2-halobiphenyl-4-yl)-cyclopropanecarboxylic acid capable of modulating γ-secretase activity without affecting other important metabolic processes such as cyclooxygenase-enzymes activity. In particular, the compound 1-(3',4'-dichloro-2-fluorobiphenyl-4-yl)cyclopropanecarboxylic acid, belonging to this class, also quoted in the literature with the experimental code CHF 5074, has been found particularly useful for treating Alzheimer disease as well as for preventing cognitive disorders.

On the other hand, drugs aimed at the treatment of C.N.S. diseases such as Alzheimer's disease, in order to efficaciously exercise their therapeutic activity, need to cross the blood-brain barrier. The passage and the distribution in the C.N.S. of polar drugs such as the carboxylic acids and their derivatives are strongly limited by the presence of said barrier.

In WO 2006/016219, pro-drugs of the 1-(2-halobiphenyl-4-yl)-cyclopropanecarboxylic acids of WO 2004/074232 have been disclosed wherein the carrier molecule is the amide of an amino acid, in particular glycinamide. However, said pro-drugs, notwithstanding that they are endowed with a good brain penetration, turned out to be rather stable and hardly release the active moiety.

Therefore, it would be highly advantageous to provide further carrier molecules to link said 1-(2-halobiphenyl-4-yl)-cyclopropanecarboxylic acids in such a way to obtain pro-drugs capable of releasing more efficiently the active moiety than those of the prior art. This problem is solved by the compounds of the present invention.

SUMMARY OF THE INVENTION

Accordingly, it is one object of the present invention to provide novel derivatives of 1-(2-halo-biphenyl-4-yl) alkanecarboxylic acids wherein the carboxylic group is linked to a residue capable of allowing the passage through the blood-brain barrier so as to release the active moiety in the brain.

It is another object of the present invention to provide novel methods for the prevention and/or treatment of neurodegenerative diseases or the treatment of cognitive function impairment by administering such a compound.

These and other objects, which will become apparent during the following detailed description, have been achieved by the inventors' discovery that compounds of formula (I):

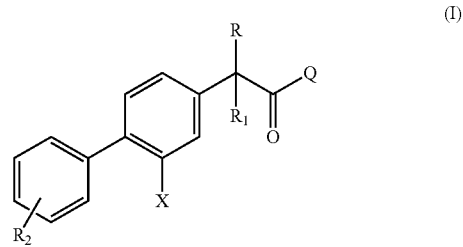

(I)

wherein:

X is a halogen selected from the group of F, Cl, Br, and I, preferably fluorine;

R and $R_1$ are the same and are straight or branched ($C_1$-$C_4$)-alkyl; otherwise they form a 3 to 6 carbon atoms saturated ring with the carbon atom to which they are linked;

$R_2$ represents one or more groups independently selected from halogen atoms, preferably chlorine; and Q is a group $Q_1$ or $Q_2$ as below represented

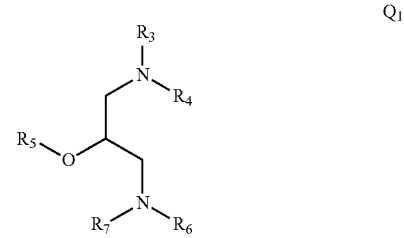

$Q_1$

-continued

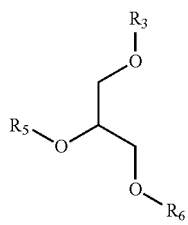

wherein:

$R_3$, $R_5$ and $R_6$ are independently $(C_1-C_4)$-alkyl, $(C_2-C_{16})$-alkanoyl, or a bond connecting the group $Q_1$ or $Q_2$ to the rest of the molecule with the condition that one and only one of $R_3$, $R_5$ and $R_6$ is a bond; and $R_4$ and $R_7$ are independently H, $(C_1-C_4)$-alkyl, or $(C_2-C_{16})$-alkanoyl, pass through the blood-brain barrier so as to release the active moiety in the brain.

Thus, in a first embodiment, the present invention provides derivatives of 1-(2-halo-biphenyl-4-yl) alkanecarboxylic acids wherein the carboxylic group is linked to a residue capable of allowing the passage through the blood-brain barrier so as to release the active moiety in the brain. Said compounds, which act as pro-drugs, have the general formula (I).

In a second embodiment, the present invention provides pharmaceutical compositions comprising a compound of general formula (I) optionally in combination with one or more pharmaceutically acceptable carriers and/or excipients.

In a third embodiment, the present invention provides processes for the preparation of compounds of general formula (I).

In a fourth embodiment, the present invention is directed to compounds of general formula (I) for use as a medicament.

In a fifth embodiment, the present invention is directed to compounds of general formula (I) for use for preventing and/or treating a neurodegenerative disease or improving cognitive function or treating cognitive function impairment.

In a sixth embodiment, the present invention provides the use of the compounds of general formula (I) in the manufacture of a medicament for preventing and/or treating a neurodegenerative disease or improving cognitive function or treating cognitive function impairment.

In a seventh embodiment, the present invention provides a method for preventing and/or treating a neurodegenerative disease or improving cognitive function or treating cognitive function impairment, which comprises administering to a subject in need thereof a therapeutically effective amount of a compound of general formula (I).

DETAILED DESCRIPTION OF THE PREFERRED EMBODIMENTS

The term "pro-drug" means a pharmaceutical compound administered in an inactive form that, upon crossing the blood-brain barrier, it is metabolized to release the active moiety in the brain in order to allow its local distribution.

The term "halogen atom" includes fluorine, chlorine, bromine, and iodine.

The term "linear or branched $(C_1-C_4)$-alkyl" means an alkyl chain in which the number of constituent carbon atoms is in the range of 1 to 4, such as methyl, ethyl, n-propyl, isopropyl, n-butyl, isobutyl, sec-butyl, and tert-butyl.

The term "3 to 6 carbon atoms saturated ring" includes cyclopropyl, cyclobutyl, cyclopentyl, and cyclohexyl rings.

The expression "$(C_2-C_{16})$-alkanoyl", refers to straight or branched, saturated or unsaturated alkanoyl groups, preferably straight and saturated, wherein the number of constituent carbon atoms is in the range of 2 to 16. Examples of said groups are acetyl, propionyl, butyryl, pentanoyl (valeryl), hexanoyl, heptanoyl, octanoyl, nonanoyl, decanoyl, undecanoyl, dodecanoyl (lauroyl), tetradecanoyl (myristoyl), pentadecanoyl, and hexadecanoyl (palmitoyl).

The term "an effective amount of a compound for preventing and/or treating a particular disease" represents the amount that is sufficient to prevent, ameliorate, or in some manner reduce, the symptoms associated with the disease.

The term "treatment" means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable.

The term "prevention" refers to the use for reducing the occurrence of the disease.

The present invention is directed to compounds of formula (I):

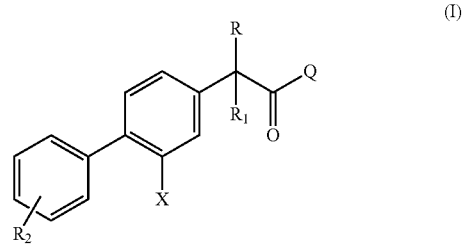

wherein:

X is a halogen selected from the group of F, Cl, Br, and I, preferably fluorine.

R and $R_1$ are the same and are straight or branched $(C_1-C_4)$-alkyl; otherwise they form a 3 to 6 carbon atom saturated ring with the carbon atom to which they are linked;

$R_2$ represents one or more groups independently selected from halogen atoms, preferably chlorine;

Q is a group $Q_1$ or $Q_2$ as below represented

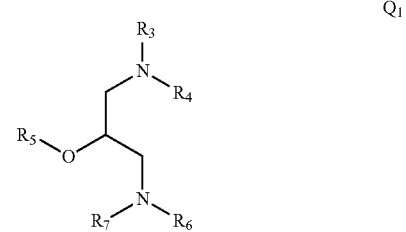

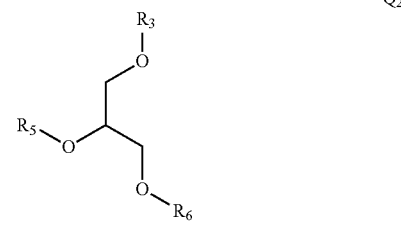

wherein:

$R_3$, $R_5$ and $R_6$ are independently $(C_1-C_4)$-alkyl, $(C_2-C_{16})$-alkanoyl, or a bond connecting the group $Q_1$ or $Q_2$ to the rest of the molecule with the condition that one and only one of $R_3$, $R_5$ and $R_6$ is a bond;

$R_4$ and $R_7$ are independently H, $(C_1-C_4)$-alkyl, or $(C_2-C_{16})$-alkanoyl.

In one embodiment, R and $R_1$ form a 3 carbon atom ring with the carbon atom to which they are linked, X is fluorine, $R_2$ is one or more chlorine atoms and Q is as defined above.

In another embodiment, R and $R_1$ are the same and both are methyl, X is fluorine, $R_2$ is one or more chlorine atoms and Q is as defined above.

In a more preferred embodiment, the compounds of general formula (I) have the following formula (Ia)

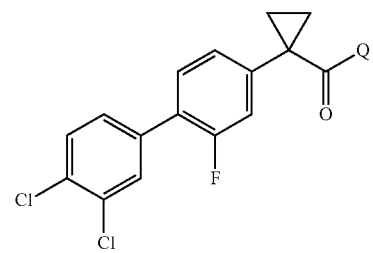

(Ia)

wherein Q is as defined above.

A particularly preferred group of compounds of general formula (I) is that of formula (Ib) in which $R_5$ is bond

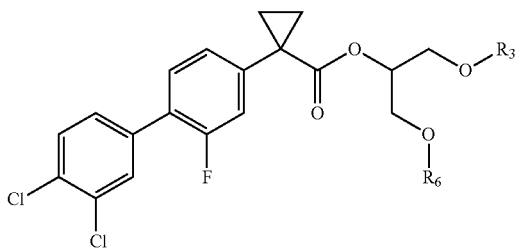

(Ib)

and wherein $R_3$ and $R_6$ are as defined above.

In one embodiment, $R_3$ and $R_6$ can be the same or different from each other, and are independently selected from ($C_2$-$C_4$)-alkanoyl, preferably acetyl, and ($C_{12}$-$C_{16}$)-alkanoyl, preferably hexadecanoyl.

Another particularly preferred group of compounds of general formula (I) is that of formula (Ic) in which $R_5$ is bond.

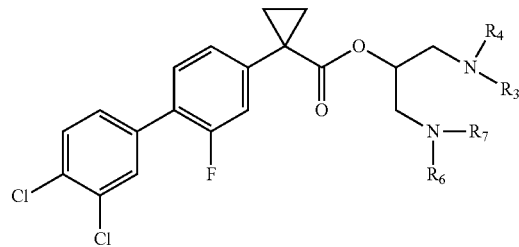

(Ic)

and wherein $R_3$, $R_4$, $R_6$ and $R_7$ are as defined above.

In one embodiment, $R_3$ and $R_6$ can be the same or different from each other, and are selected from ($C_2$-$C_4$)-alkanoyl, preferably acetyl, while $R_4$ and $R_7$ can be the same or different from each other, and are independently selected from H or ($C_1$-$C_4$)-alkyl, preferably methyl.

A further particularly preferred group of compounds of general formula (I) is that of formula (Id) in which $R_6$ is bond.

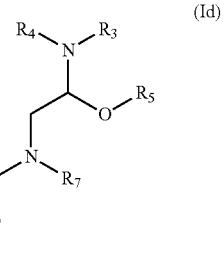

(Id)

and wherein $R_3$, $R_4$, $R_5$ and $R_7$ are as defined above.

In one embodiment, $R_3$ and $R_5$ can be the same or different from each other, and are selected from ($C_2$-$C_4$)-alkanoyl, preferably acetyl, while $R_4$ and $R_7$ can be the same or different from each other, and are independently selected from H or ($C_1$-$C_4$)-alkyl, preferably methyl.

It will be apparent to those skilled in the art that the compounds of general formula (I) may contain asymmetric centers.

Therefore the invention encompasses the optical stereoisomers and mixtures thereof.

According to specific embodiments, the present invention provides the compounds reported below:

| Compound | Compound structure | Chemical name |
| --- | --- | --- |
| C1 | 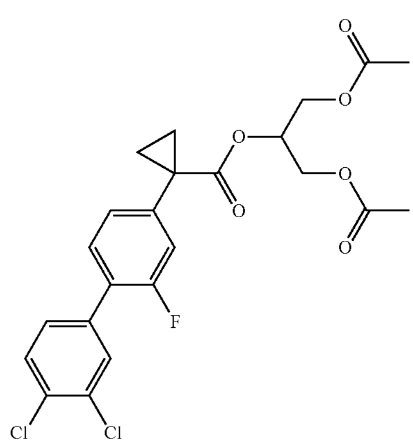 [SMILES: CC(=O)OCC(COC(C)=O)OC(=O)C1(c2ccc(-c3ccc(Cl)c(Cl)c3)c(F)c2)CC1] | 1-(3',4'-Dichloro-2-fluorobiphenyl-4-yl)cyclopropanecarboxylic acid 2-acetoxy-1-acetoxymethylethyl ester |

-continued

| Compound | Compound structure | Chemical name |
|---|---|---|
| C2 | 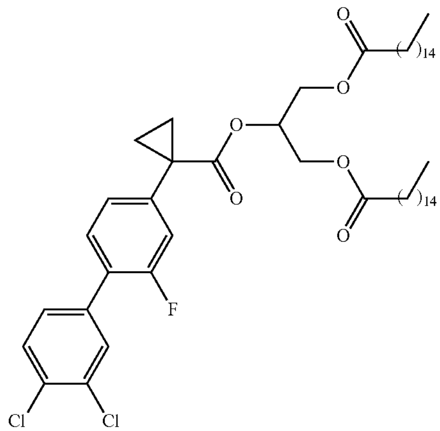 | 1-(3',4'-Dichloro-2-fluorobiphenyl-4-yl)cyclopropanecarboxylic acid 2-hexadecanoyloxy-1-hexadecanoyloxymethylethyl ester |
| C3 | 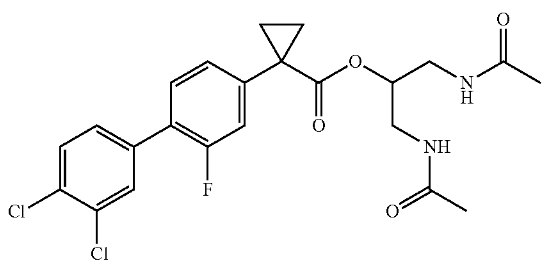 [SMILES: CC(=O)NCC(CNC(C)=O)OC(=O)C1(c2ccc(-c3ccc(Cl)c(Cl)c3)c(F)c2)CC1] | 1-(3',4'-Dichloro-2-fluorobiphenyl-4-yl)cyclopropanecarboxylic acid 2-acetylamino-1-(acetylaminomethyl)ethyl ester |
| C4 | 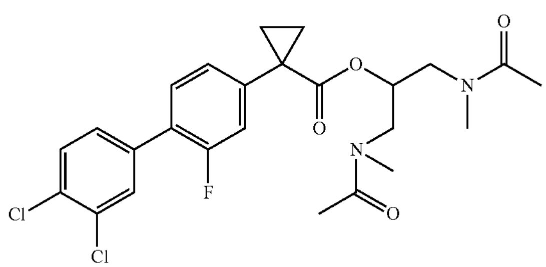 [SMILES: CC(=O)N(C)CC(CN(C)C(C)=O)OC(=O)C1(c2ccc(-c3ccc(Cl)c(Cl)c3)c(F)c2)CC1] | 1-(3',4'-Dichloro-2-fluorobiphenyl-4-yl)cyclopropanecarboxylic acid 2-(acetylmethylamino)-1-[(acetylmethylamino)methyl]ethyl ester |
| C5 | 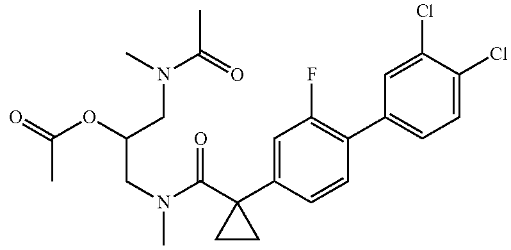 [SMILES: CC(=O)OC(CN(C)C(C)=O)CN(C)C(=O)C1(c2ccc(-c3ccc(Cl)c(Cl)c3)c(F)c2)CC1] | Acetic acid 2-(acetylmethylamino)-1-({[1-(3',4'-dichloro-2-fluorobiphenyl-4-yl)-cyclopropanecarbonyl]methyl amino}methyl)ethyl ester |

The 1-(2-halo-biphenyl-4-yl) alkanecarboxylic acid derivative, i.e. the active moiety of the compounds of the invention, may be prepared according to the methods disclosed in WO 2004/074232, WO 2009/149797, or WO 2011/015287, all of which are incorporated herein by reference in their entireties.

The compounds of formula (I) may in turn be prepared according to methods known to the person skilled in the art.

Scheme 1

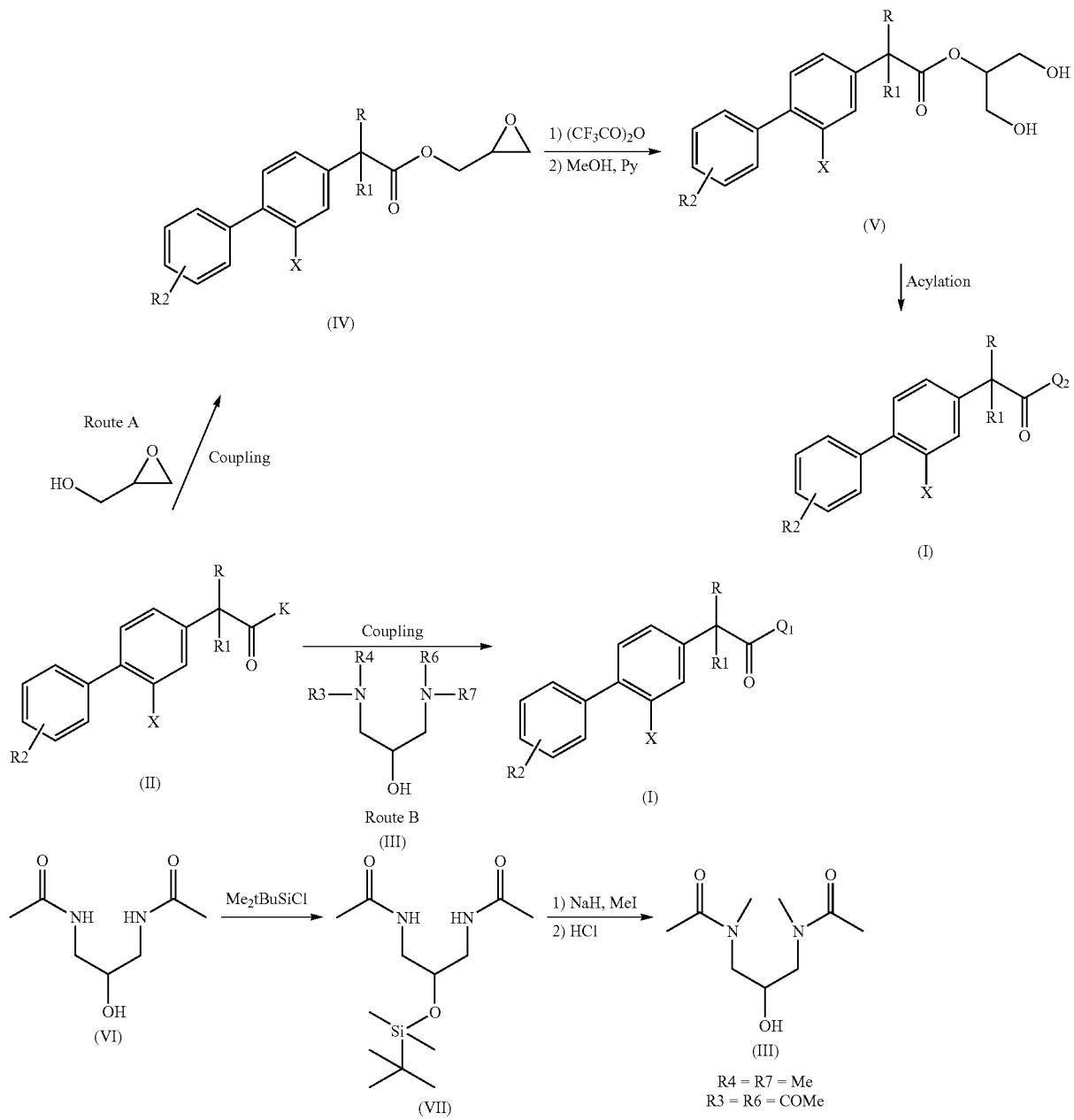

For exemplary purposes, some of the processes which may be used are described below and reported in Scheme 1.

Procedures for the Preparation of Compounds of Formula (I).

As reported above, compounds of formula (I) may be prepared according to standard procedures extensively reported in the literature. Most preferably, the compounds of general formula (I) may be prepared according to two different routes: A and B.

Route A. Compounds of formula (IV) may be synthesized starting from compounds of formula (II), in which K may be either a hydroxyl group or a halide, such as chlorine, and glycidol according to procedures readily available to those skilled in the art (a survey of the suitable reactions is given by Carey, F. A. and Sundeberg, R. J. Advanced Organic Chemistry, Third Edition (1990), Plenum Press, New York and London, pg 145, which is incorporated herein by reference in its entirety).

Alternative one. In a typical procedure, compounds (IV) may be prepared by condensation between glycidol and acid (II) (K=OH) under standard coupling conditions. For instance, treatment of the acid (II) (K=OH) with one or more equivalents of a commercially available condensing agent such as a carbodiimide, e.g. N,N'-dicyclohexylcarbodiimide (DCC) or 1-(3-dimethylamino)propyl)-3-ethylcarbodiimide hydrochloride (EDC), and the like, followed by reaction of the activated intermediate with glycidol results in the formation of compounds (IV). An organic base such as dimethylaminopyridine (DMAP) may be also present in the reaction mixture. The activated intermediate may be either isolated, or pre-formed or generated in situ. Suitable solvents for the coupling include, but are not limited to, halocarbon solvents (e.g. dichloromethane), tetrahydrofuran, dioxane and acetonitrile. The reaction proceeds at a temperature range from 0° C. up to 170° C., for a time in the range of about 1 hour up to 72 hours. The reaction may be carried out under conventional heating (using an oil bath) or under microwave irradiation. The reaction may be conducted either in an open vessel or in a sealed tube.

Alternative two. In the case where K is halogen, such as chlorine, glycidol is reacted with the suitable acyl halide (II), using methods that are readily apparent to those skilled in the art. This reaction is performed in a temperature range from 0° C. to 130° C. over a period of 1 hour up to 74 hours. The reaction may be conducted under conventional heating (using an oil bath) or under microwave heating. The reaction may be carried out in an open vessel or in a sealed tube.

In some embodiments of the present invention, the needed acyl halide (II) may be readily prepared from the corresponding acid (II) (K=OH). This activation may be effected according to one of the standard procedures reported in the literature. For instance, treatment of acid (II) (K=OH) with one or more equivalents of oxalyl chloride in the presence of a catalytic amount of dimethylformamide (DMF) in a halocarbon solvent, such as dichloromethane, at temperature ranging form 0° C. to 35° C., affords the required acyl chloride (II) (K=Cl).

Alternative three. Alternatively, acylation of glycidol to give compounds of general formula (IV) may be accomplished using procedures converting in situ the acid (II) (K=OH) into the corresponding acyl halide. For example, glycidol is reacted with acid (II) (K=OH) in presence of triphenylphosphine and a halocarbon solvent such as carbon tetrachloride at room temperature, in a maximum period of time of 16 hours (see Lee, J. B. J. Am. Chem. Soc., 1966, 88, 3440, which is incorporated herein by reference in its entirery).

Alternative four. In another process for the preparation of the compounds of the present invention, acid (II) (K=OH) may be activated with other commercially available activating agents such as bromotripyrrolidinophosphonium hexafluorophosphate (PyBrOP) or carbonylimidazole, in the suitable aprotic solvent (e.g. dichloromethane, tetrahydrofuran), at about room temperature. Subsequent reaction of the activated intermediate with glycidol provides the desired compound of formula (IV). The reaction usually proceeds at room temperature.

Alternative five. In another process for the preparation of the compounds of the present invention, compounds (IV) can be efficiently prepared through the condensation between acid (II) (K=OH) and glycidol under typical Mitsunobu conditions (see Kumara Swamy, K. C., Chem. Rev. 2009, 109, 2551-2651, which is incorporated herein by reference in its entirety). For example, acid (II) and glycidol are reacted in presence of a phosphine (e.g. triphenylphosphine) and an azadicarboxylate ester (e.g. diethyl azodicarboxylate or diisopropyl azodicarboxylate) in an aprotic solvent such as tetrahydrofuran. The reaction typically proceeds at a temperature ranging from 0° C. up to 100° C., for a time in the range of about 30 minutes up to 72 hours.

Glycidyl ester of formula (IV) may be converted into compound of formula (V) by a trifluoroacetic anhydride-catalyzed opening of the oxirane system of glycidyl ester with a simultaneous migration of the acyl group, as described by Stomatov S. et al. in Tetrahedron, 2005, 61(15), 3659, which is incorporated herein by reference in its entirety. Following hydrolysis of trifluoroacetate groups with pyridine in methanol affords compound of formula (V) which may be converted into final compound of formula (I) by acylation with the appropriate acyl chloride or anhydride (e.g. acetic anhydride).

Route B. Compounds of formula (II), in which K may be either a hydroxyl group or a halide such as chlorine, may be reacted with an agent of general formula (III), in which $R_3$, $R_4$, $R_6$ and $R_7$ are as defined above according to procedures readily available to those skilled in the art (a survey of the suitable reactions is given by Carey, F. A. and Sundeberg, R. J. Advanced Organic Chemistry, Third Edition (1990), Plenum Press, New York and London, pg 145, which is incorporated herein by reference in its entirety).

Alternative one. In a typical procedure compounds of formula (I) may be prepared by condensation between compounds (III) and acid (II) (K=OH) under standard coupling conditions. For instance, treatment of the acid (II) (K=OH) with one or more equivalents of a commercially available condensing agent such as a carbodiimide, e.g. 1-(3-dimethylamino)propyl)-3-ethylcarbodiimide hydrochloride (EDC), and the like, for example in the presence of N-hydroxybenzotriazole (HOBt) followed by reaction of the activated intermediate with (III), results in the formation of a compound of formula (I). An organic base such as triethylamine may be optionally present in the reaction mixture. The activated intermediate may be either isolated, or pre-formed or generated in situ. Suitable solvents for the coupling include, but are not limited to, halocarbon solvents (e.g. dichloromethane), tetrahydrofuran, dioxane and acetonitrile. The reaction proceeds at a temperature range from 0° C. up to 170° C., for a time in the range of about 1 hour up to 72 hours. The reaction may be carried out under conventional heating (using an oil bath) or under microwave irradiation. The reaction may be conducted either in an open vessel or in a sealed tube.

Alternative two. In the case where K is halogen such as chlorine, intermediate (III) is reacted with the suitable acyl halide (II), using methods that are readily apparent to those skilled in the art.

The reaction may be promoted by a base such as triethylamine, pyridine and 4-dimethylaminopyridine, in a suitable solvent (e.g. dichloromethane). This reaction is performed in a temperature range from 0° C. to 130° C. over a period of 1 hour up to 74 hours. The reaction may be conducted under conventional heating (using an oil bath) or under microwave heating. The reaction may be carried out in an open vessel or in a sealed tube.

In some embodiments of the present invention, the needed acyl halide (II) may be readily prepared from the corresponding acid (II) (K=OH). This activation may be effected according to one of the standard procedures reported in the literature. For instance, treatment of acid (II) (K=OH) with one or more equivalents of oxalyl chloride in the presence of a catalytic amount of dimethylformamide (DMF) in a halocarbon solvent, such as dichloromethane, at temperature ranging form 0° C. to 35° C., affords the required acyl chloride (II) (K=Cl).

Alternative three. Alternatively, acylation of compounds (III) to give compounds of general formula (I) may be accomplished using procedures which convert in situ the acid (II) (K=OH) into the corresponding acyl halides. For example, intermediate (III) is reacted with acids (II) (K=OH) in presence of triphenylphosphine and a halocarbon solvent such as carbon tetrachloride at room temperature, in a maximum period of time of 16 hours (see Lee, J. B. J. Am. Chem. Soc., 1966, 88, 3440, which is incorporated herein by reference in its entirety).

Alternative four. In another process for the preparation of the compounds of the present invention, acid (II) (K=OH) may be activated with other commercially available activating agents such as bromotripyrrolidinophosphonium hexafluorophosphate (PyBrOP) or carbonylimidazole, in the suitable aprotic solvent (e.g. dichloromethane, tetrahydrofuran), at room temperature. Subsequent reaction of the activated intermediate with compounds (III) provides the desired compound of formula (I). The reaction may optionally require the use of an organic base such as diisopropylethylamine and usually proceeds at room temperature.

Alternative five. In another process, the compounds of formula (I) may be efficiently prepared by the condensation between acids (II) (K=OH) and alcohol (III) under typical Mitsunobu conditions (see Kumara Swamy, K. C., Chem. Rev. 2009, 109, 2551-2651, which is incorporated herein by reference in its entirety). For example, acids (II) and alcohol (III) are reacted in presence of a phosphine (e.g. triphenylphosphine) and an azadicarboxylate ester (e.g. diethyl azodicarboxylate or diisopropyl azodicarboxylate) in an aprotic solvent such as tetrahydrofuran. The reaction typically proceeds at temperature range from 0° C. up to 100° C., for a time in the range of about 30 minutes up to 72 hours.

The obtained products may be further functionalized. For example, the secondary amido groups may be further functionalized by alkylation with a suitable alkylating agent, converting them into a tertiary amido group ($R_3$ and/or $R_7$ are converted into alkyl groups). For this purpose, a suitable alkyl halide (e.g. methyl iodide or ethyl bromide) may be used. This alkylation can be carried out following one of the standard procedures commonly reported in literature (for instance, Zawadzki, S. et al., Synthesis, 1979, 549; Yamawaki, J. et al., Chem. Lett., 1981, 1143; Sukata, K. et al., Bull. Chem. Soc. Jpn., 1985, 58, 838, all of which are incorporated herein by reference in their entireties). In a typical procedure, the alkylation reaction is promoted by the presence of a base, for instance an inorganic base such as potassium or cesium carbonate or sodium hydride.

The reaction is generally performed in a suitable solvent (e.g. THF, DMF, $CH_3CN$, or acetone) in a temperature range from about 0° C. to about 130° C. over a period of about 1 hour up to about 74 hours. The reaction may be conducted under conventional heating (using an oil bath) or under microwave heating. The reaction may be carried out in an open vessel or in a sealed tube.

In one embodiment of the present invention, a compound of formula (III) ($R_4=R_7$=methyl, $R_3=R_6=COCH_3$) may be synthesized starting from compound of formula (VI) by protection of the hydroxyl group as dimethyltertbutylsilyl ether, alkylation with methyl iodide and sodium hydride and deprotection of the silyl ether protecting group with hydrochloric acid (see Scheme 1). A compound (VI) can in turn be synthesized starting from 1,3-diaminopropan-2-ol, as described in J. Org. Chem., 2000, 65(4), 1200, which is incorporated herein by reference in its entirety.

A further object of the present invention concerns pharmaceutical compositions comprising at least one compound of formula (I). Said compound may be combined with one or more pharmaceutically acceptable carriers or excipients.

The pharmaceutically acceptable carriers or excipients may be advantageously selected from the group consisting of, diluents, wetting agents, emulsifying agents, binders, coatings, fillers, glidants, lubricants, disintegrants, preservatives, stabilizers, surfactants, pH buffering substances, flavouring agents and the like. Comprehensive guidance on pharmaceutical excipients is given in Remington's Pharmaceutical Sciences Handbook, XVII Ed. Mack Pub., N.Y., U.S.A, which is incorporated herein by reference in its entirety.

The pharmaceutical compositions may comprise further active ingredients useful for the treatment of neurodegenerative diseases such as acetylcholine-esterase inhibitors.

The compounds of the present invention can be formulated for administration by any convenient route, e.g. by oral, parenteral, topical, inhalation, buccal, nasal, rectal, and transdermal administration. Suitable dosage forms can include tablets, capsules, lozenges, suppositories, solutions, emulsions, suspensions, syrups, ointments, creams, oils, and powders.

Preferably, the pharmaceutical compositions of the present invention will be administered orally using appropriate dosage forms, such as capsules, tablets, caplets etc, more preferably tablets.

The dosage of the compounds of the present invention and the duration of the treatment can vary within certain limits depending on the type of patient (weight, sex, subject age), the mode of administration and the severity advancement of the disease to be treated. A person skilled in the art may determine the optimal therapeutically effective amount and the regimen for each patient and thereby define the appropriate dosage and the duration of the treatment. Typically, the daily dosage might fall within the range of 10 mg to 1500 mg, preferably from 100 to 800 mg.

The compounds of the present invention may be used for preventing and/or treating a neurodegenerative disease, improving cognitive function and treating cognitive function impairment.

Preferably, the neurodegenerative disease is an amyloidogenic disease, such as Alzheimer's disease or transthyretin (TTR) amyloidosis, more preferably Alzheimer's disease.

The cognitive function impairment is typically associated with disorders such as autism, dyslexia, attention deficit hyperactivity disorder, schizophrenia, obsessive compulsive disorders, psychosis, bipolar disorders, depression, Tourette's syndrome and disorders of learning in children, adolescents and adults, Age Associated Memory Impairment, Age Associated Cognitive Decline, Parkinson's Disease, Down's Syndrome, traumatic brain injury Huntington's Disease, Progressive Supranuclear Palsy (PSP), HIV, stroke, vascular diseases, Pick's or Creutzfeldt-Jacob diseases, multiple sclerosis (MS). In a preferred embodiment, the impairment of cognitive function is caused by, or attributed to, Alzheimer's disease. In a more preferred embodiment, the impairment of cognitive function is caused by, or attributed to, mild cognitive impairment (MCI).

Other features of the invention will become apparent in the course of the following descriptions of exemplary embodiments which are given for illustration of the invention and are not intended to be limiting thereof.

EXAMPLES

Legend

I=intermediates;

C=compounds;

$^1$H NMR: s=singlet; d=doublet; t=triplet; q=quartet; dd=doublet of doublets; m=multiplet; br=broad

Example 1

Preparation of 1-(3',4'-dichloro-2-fluorobiphenyl-4-yl)cyclopropane carboxylic acid 2-acetoxy-1-acetoxymethylethyl ester (C1)

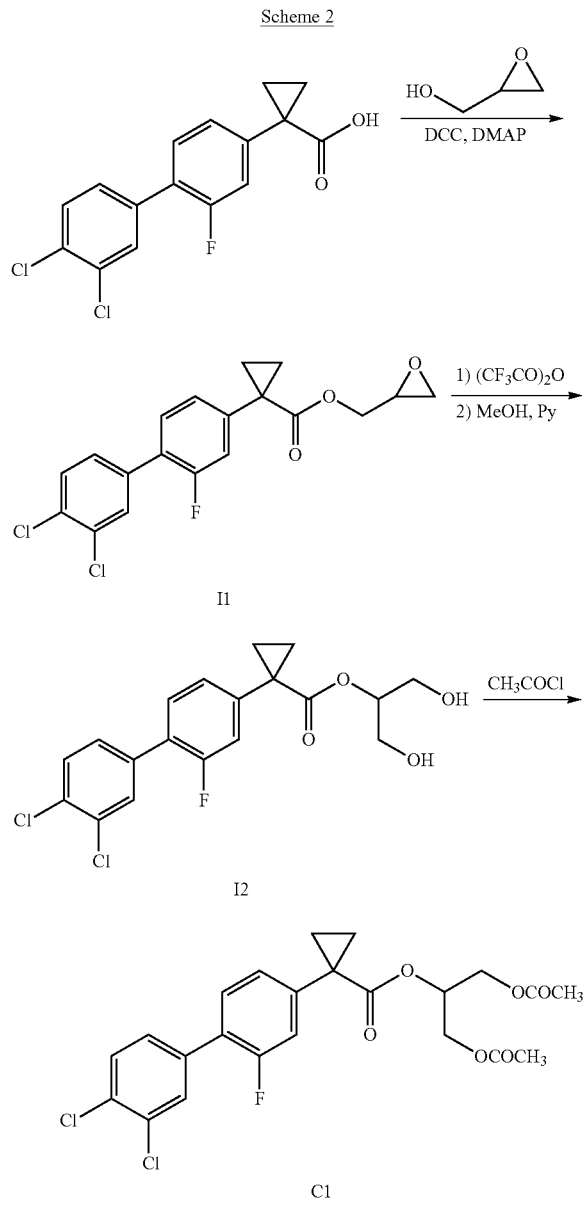

Scheme 2

Preparation of 1-(3',4'-dichloro-2-fluorobiphenyl-4-yl)cyclopropane carboxylic acid oxiranylmethyl ester (I1)

1-(3',4'-Dichloro-2-fluorobiphenyl-4-yl)cyclopropanecarboxylic acid (2.00 g, 6.15 mmol), dicyclohexylcarbodiimide (DCC, 2.54 g, 12.30 mmol), 4-dimethyl-aminopyridine (DMAP, 0.075 g, 0.614 mmol), and oxiran-2-ylmethanol (0.490 ml, 7.38 mmol) were dissolved in dry DCM (40 mL). The reaction mixture was stirred at room temperature (r.t.) overnight, then it was filtered and the filtrate was evaporated to dryness to afford 4.4 g of crude. The crude was purified by gradient flash chromatography eluting with petroleum ether/EtOAc (from 97/3 to 90/10 v/v) to afford 1-(3',4'-dichloro-2-fluorobiphenyl-4-yl)cyclopropane carboxylic acid oxiranylmethyl ester (1.0 g, 42.6% yield).

Preparation of 1-(3',4'-dichloro-2-fluorobiphenyl-4-yl)cyclopropane carboxylic acid 2-hydroxy-1-hydroxymethylethyl ester (I2)

1-(3',4'-Dichloro-2-fluorobiphenyl-4-yl)cyclopropane carboxylic acid oxiranylmethyl ester (1.0 g, 2.62 mmol) was dissolved in dry DCM (25 mL), and the solution was cooled at −20° C. To this solution 2,2,2-trifluoroacetic anhydride (1.46 mL, 10.49 mmol) in dry DCM (25 mL) was added, and the reaction mixture was kept at r.t. for 2 hours. All the volatile components were removed under reduced pressure, and traces of trifluoroacetic anhydride were removed by co-evaporation with toluene (2×100 mL) to afford crude 1-(3',4'-dichloro-2-fluorobiphenyl-4-yl)cyclopropanecarboxylic acid 2-(2,2,2-trifluoro-acetoxy)-1-(2,2,2-trifluoro-acetoxymethyl)ethyl ester (1.4 g, 2.368 mmol) as a colourless oil. 1-(3',4'-Dichloro-2-fluorobiphenyl-4-yl)cyclopropanecarboxylic acid 2-(2,2,2-trifluoro-acetoxy)-1-(2,2,2-trifluoro-acetoxymethyl)ethyl ester (0.9 g, 1.522 mmol) was dissolved in a mixture of pentane/$CH_2Cl_2$ (3/1 v/v; 10 mL), and the solution was cooled at −20° C. To this solution, pyridine (1.231 mL, 15.22 mmol) and methanol (0.925 mL, 22.83 mmol) dissolved in a mixture of pentane/DCM (3/1 v/v; 10 mL) were added. The reaction mixture was allowed to warm to r.t. and stirred at r.t. for 1 hour and 45 minutes. The solvent was removed under reduced pressure, and the residue was dried under vacuum for 1 hour to obtain crude 1-(3',4'-dichloro-2-fluorobiphenyl-4-yl)cyclopropane carboxylic acid 2-hydroxy-1-hydroxymethylethyl ester (0.61 g, quantitative yield) which was used as such in the next reaction.

Preparation of 1-(3',4'-dichloro-2-fluorobiphenyl-4-yl)cyclopropane carboxylic acid 2-acetoxy-1-acetoxymethylethyl ester (C1)

A solution of acetyl chloride (0.435 mL, 6.11 mmol) in dry DCM (10 mL) was added to a solution of 1-(3',4'-dichloro-2-fluorobiphenyl-4-yl)cyclopropane carboxylic acid 2-hydroxy-1-hydroxymethylethyl ester (0.61 g, 1.53 mmol) and pyridine (2.47 mL, 30.6 mmol) in dry DCM (10 mL). The reaction mixture was stirred for 30 minutes at r.t., then the solvent was evaporated under reduced pressure and the residue was purified by flash chromatography (eluent petroleum ether/EtOAc=85/15 v/v) to afford 1-(3',4'-dichloro-2-fluorobiphenyl-4-yl)cyclopropane carboxylic acid 2-acetoxy-1-acetoxymethylethyl ester (460 mg, 62% yield) as a colourless oil.

$^1$H NMR (300 MHz, $CDCl_3$) ppm: 7.66 (dd, 1H), 7.53 (d, 1H), 7.40 (m, 1H), 7.35 (t, 1H), 7.11-7.23 (m, 2H), 5.22 (m, 1H), 4.33 (dd, 2H), 4.09 (dd, 2H), 2.06 (s, 6H), 1.65-1.74 (m, 2H), 1.19-1.34 (m, 2H).

LC-MS (ESI POS): 504.84 (M*Na+).

Example 2

Preparation of 1-(3',4'-dichloro-2-fluorobiphenyl-4-yl)cyclopropane carboxylic acid 2-hexadecanoyloxy-1-hexadecanoyloxymethylethyl ester (C2)

Scheme 3

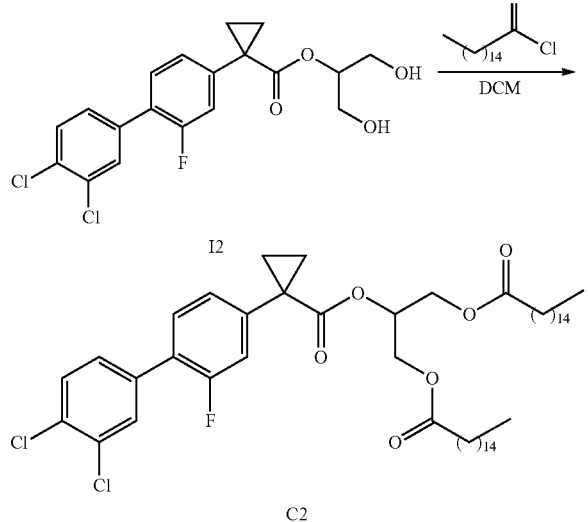

A solution of palmitoyl chloride (2.06 g, 7.51 mmol) in dry DCM (25 mL) was added to a solution of 1-(3',4'-dichloro-2-fluorobiphenyl-4-yl)cyclopropane carboxylic acid 2-hydroxy-1-hydroxymethylethyl ester (1.0 g, 2.50 mmol) and pyridine (4.05 mL, 50.1 mmol) in dry DCM (25 ml) and stirred at r.t. for 3 hours. The solvent was removed under reduced pressure, and the residue was triturated with petroleum ether. The solid was filtered off and the filtrate was evaporated under reduced pressure to afford 2.3 g of crude, which was purified by flash chromatography eluting with petroleum ether/EtOAc=95/5 v/v to afford 1-(3',4'-dichloro-2-fluorobiphenyl-4-yl)cyclopropanecarboxylic acid 2-hexadecanoyloxy-1-hexadecanoyloxymethylethyl ester (410 mg, 19% yield) as a white solid.

$^1$H NMR (300 MHz, CDCl$_3$) ppm: 7.66 (dd, 1H), 7.52 (d, 1H), 7.40 (m, 1H), 7.34 (t, 1H), 7.12-7.23 (m, 2H), 5.24 (tt, 1H), 4.32 (dd, 2H), 4.09 (dd, 2H), 2.30 (t, 4H), 1.66-1.75 (m, 2H), 1.57-1.65 (m, 4H), 1.28 (m, 50H), 0.90 (t, 6H).

LC-MS (ESI POS): 897.33 (M*Na+).

Example 3

Preparation of 1-(3',4'-Dichloro-2-fluorobiphenyl-4-yl)cyclopropane carboxylic acid 2-acetylamino-1-(acetylaminomethyl)-ethyl ester (C3)

Scheme 4

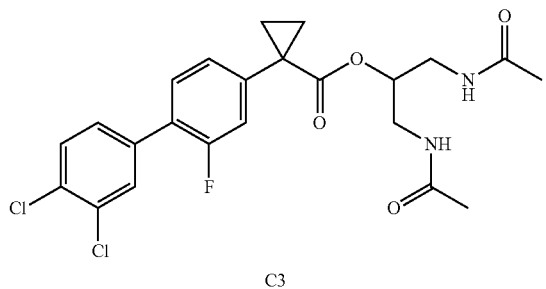

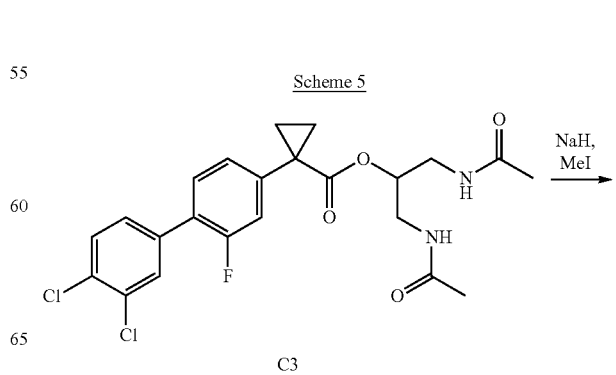

1-(3',4'-Dichloro-2-fluorobiphenyl-4-yl)cyclopropanecarboxylic acid (0.30 g, 0.92 mmol) was dissolved in dry DCM (30 mL); two drops of DMF and oxalyl chloride (78 uL, 0.92 mmol) were added; and the reaction mixture was stirred at r.t. under nitrogen atmosphere for 30 minutes. Additional oxalyl chloride (39 uL, 0.46 mmol) was added and the reaction was stirred for 15 minutes. This solution was added dropwise to a solution of N-(3-acetylamino-2-hydroxypropyl)acetamide (synthesized as reported on J. Org. Chem., 2000, 65(4), 1200, which is incorporated herein by reference in its entirety) and triethylamine (385 uL, 2.76 mmol) in dry DCM (2 mL) and dry DMF (2 mL). 4-Dimethylaminopyridine (34 mg, 0.28 mmol) and dry pyridine (1.5 mL) were added, and the reaction mixture was stirred overnight at r.t. The reaction mixture was extracted with DCM/H$_2$O, and the organic phase was washed with brine, dried over sodium sulphate, filtered and evaporated to dryness. The residue was purified by gradient flash chromatography (eluent DCM to DCM/methanol 97/3 v/v) affording the title compound which was further purified by preparative HPLC to obtain 1-(3',4'-dichloro-2-fluorobiphenyl-4-yl)cyclopropanecarboxylic acid 2-acetylamino-1-(acetylaminomethyl)ethyl ester (105 mg, 24% yield) as a white solid.

$^1$H NMR (300 MHz, DMSO-d6) ppm: 7.84 (t, 2H), 7.81 (dd, 1H), 7.75 (d, 1H), 7.56 (m, 1H), 7.50 (d, 1H), 7.24-7.35 (m, 2H), 4.67-4.88 (m, 1H), 3.20-3.25 (m, 2H), 3.04-3.17 (m, 2H), 1.82 (s, 6H), 1.54-1.64 (m, 2H), 1.20-1.31 (m, 2H).

LC-MS (ESI POS): 480.99 (MH+).

Example 4

Preparation of 1-(3',4'-dichloro-2-fluorobiphenyl-4-yl)cyclopropane carboxylic acid 2-acetylmethylamino-1-(acetylmethylaminomethyl)ethyl ester (C4, first method)

Scheme 5

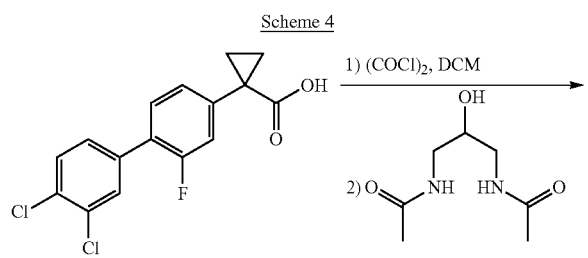

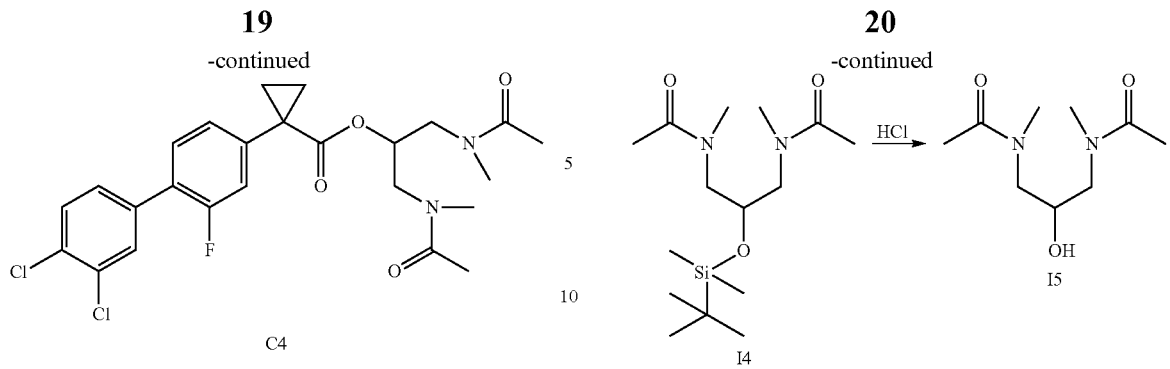

C4

To a solution of 1-(3',4'-dichloro-2-fluorobiphenyl-4-yl)cyclopropane carboxylic acid 2-acetylamino-1-(acetylaminomethyl)ethyl ester (400 mg, 0.831 mmol), and methyl iodide (0.416 mL, 6.65 mmol) in DMF (6 mL), NaH (60% dispersion in mineral oil, 80 mg, 1.994 mmol) was added at r.t. under nitrogen atmosphere and the reaction was stirred at r.t. for 1 hour. Additional methyl iodide (0.208 mL, 3.32 mmol) and NaH (60% in mineral oil, 19.94 mg, 0.499 mmol) were added, and the reaction was stirred at r.t. for 1 hour. The solution was diluted with EtOAc and washed with sat. NH$_4$Cl solution, dried with Na$_2$SO$_4$, filtered and concentrated to dryness. The crude thus obtained was purified by silica gel flash chromatography (DCM:methanol 99:1 v/v) affording 1-(3',4'-dichloro-2-fluorobiphenyl-4-yl)cyclopropane carboxylic acid 2-acetylmethylamino-1-(acetylmethylaminomethyl)ethyl ester (240 mg, 57% yield) as a pale yellow glassy gum.

$^1$H NMR (300 MHz, DMSO-d6, 353K) ppm: 7.76 (dd, 1H), 7.71 (d, 1H), 7.54 (m, 1H), 7.51 (t, 1H), 7.16-7.34 (m, 2H), 5.24 (br. s., 1H), 3.51 (br. s., 2H), 3.33 (dd, 2H), 2.85 (br. s., 6H), 1.93 (br. s., 6H), 1.46-1.66 (m, 2H), 1.14-1.38 (m, 2H).

LC-MS (ESI POS): 509.15 (MH+).

Example 5

Preparation of 1-(3',4'-dichloro-2-fluorobiphenyl-4-yl)cyclopropane carboxylic acid 2-acetylmethylamino-1-(acetylmethylaminomethyl)ethyl ester (C4, second method)

Scheme 6

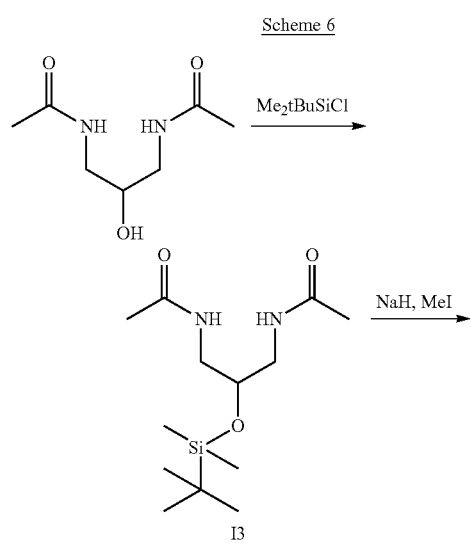

Preparation of N-[3-acetylamino-2-(tert-butyldimethylsilanyloxy)propyl]acetamide (I3)

To a solution of N-(3-acetylamino-2-hydroxypropyl)acetamide (synthesized as described in J. Org. Chem., 2000, 65(4), 1200, which is incorporated herein by reference in its entirety) (741 mg, 4.25 mmol) and 1H-imidazole (579 mg, 8.51 mmol) in dry DMF (17 mL), a solution of tert-butylchlorodimethylsilane (962 mg, 6.38 mmol) in dry DMF (8 mL) was added dropwise, and the reaction was stirred at r.t. overnight. The reaction was portioned between H$_2$O/Et$_2$O, the phases were separated and the aqueous layer was washed twice with Et$_2$O and three times with EtOAc. All the organics were combined, dried over Na$_2$SO$_4$, filtered and concentrated, affording N-[3-acetylamino-2-(tert-butyldimethylsilanyloxy) propyl]acetamide (1140 mg, 3.95 mmol, 93% yield) as off-white solid.

$^1$H NMR (300 MHz, DMSO-d6) ppm: 7.73 (t, 2H), 3.72 (m, 1H), 2.94-3.18 (m, 4H), 1.80 (s, 6H), 0.86 (s, 9H), 0.04 (s, 6H).

Preparation of N-[3-(acetylmethylamino)-2-(tert-butyldimethyl silanyloxy)propyl]-N-methylacetamide (I4)

To a solution of N-[3-acetylamino-2-(tert-butyldimethylsilanyloxy) propyl]acetamide (1135 mg, 3.934 mmol) and iodomethane (0.952 mL, 15.3 mmol) under nitrogen atmosphere, in THF (24 mL), at 0° C., sodium hydride (60% dispersion in mineral oil, 368 mg, 9.21 mmol) was added in portions. The reaction was then allowed to warm to r.t. and stirred for 2.5 hours. Additional iodomethane (0.49 mL, 7.87 mmol) and sodium hydride (60% dispersion in mineral oil, 94.4 mg, 2.36 mmol) were added, and the reaction was stirred at r.t. overnight. The reaction was diluted with EtOAc and washed with H₂O and brine, then the organic layer was dried with Na₂SO₄, filtered and concentrated to dryness affording 1.24 g of crude N-[3-(acetylmethylamino)-2-(tert-butyldimethylsilanyloxy)propyl]-N-methylacetamide that was purified by silica gel flash chromatography (DCM:methanol 95:5 v/v) affording N-[3-(acetylmethylamino)-2-(tert-butyldimethylsilanyloxy)propyl]-N-methylacetamide (1.17 g, 94% yield) as dark-yellow oil.

$^1$H NMR (300 MHz, DMSO-d6) ppm: 3.98-4.19 (m, 1H), 3.09-3.57 (m, 4H), 3.00 and 3.03 (s, 3H), 2.78 and 2.83 (s, 3H), 1.96, 2.00 and 2.03 (s, 6H), 0.86 and 0.87 (s, 9H), −0.03 (m, 6H).

Preparation of N-[3-(acetylmethylamino)-2-hydroxypropyl]-N-methylacetamide (I5)

To a solution of N-[3-(acetylmethylamino)-2-(tert-butyldimethyl silanyloxy)propyl]-N-methylacetamide (1.12 g, 3.54 mmol) in methanol (23 mL), hydrogen chloride 4M dioxane solution (0.357 mL, 1.426 mmol) was added dropwise at 0° C. and the reaction was stirred at r.t. overnight. Solvent was evaporated and the residue triturated with petroleum ether and decanted. The oil obtained after trituration was dried under vacuum affording N-[3-(acetylmethylamino)-2-hydroxypropyl]-N-methylacetamide (681 mg, 95% yield).

$^1$H NMR (300 MHz, DMSO-d6) ppm: 3.73-3.97 (m, 1H), 3.05-3.58 (m, 4H), 3.00 and 3.03 (s, 3H), 2.80 and 2.82 (s, 3H), 1.91-2.04 (m, 6H).

Preparation of 1-(3',4'-dichloro-2-fluorobiphenyl-4-yl)cyclopropane carboxylic acid 2-acetylmethylamino-1-(acetylmethylaminomethyl)ethyl ester (C4)

To a suspension of 1-(3',4'-dichloro-2-fluorobiphenyl-4-yl)cyclopropane carboxylic acid (77 mg, 0.237 mmol) in DCM (2.6 mL) containing one drop of DMF, under nitrogen atmosphere and cooled to 0° C., oxalyl dichloride (0.040 mL, 0.473 mmol) was added dropwise and the reaction was stirred at r.t. for 20 minutes. Solvent was evaporated, and crude acyl chloride was dried under vacuum. The acyl chloride thus obtained was dissolved in DCM (1 mL) and added dropwise at 0° C. to a solution of N-[3-(acetylmethylamino)-2-hydroxypropyl]-N-methylacetamide (I5) (31.9 mg, 0.158 mmol) and triethylamine (0.099 mL, 0.710 mmol) in DCM (2 mL), under nitrogen atmosphere. The reaction was stirred at r.t. overnight; DMAP (6.3 mg, 0.052 mmol) and additional triethylamine (0.022 mL, 0.158 mmol) were added, and the reaction was heated at 40° C. for 3 hours. The reaction mixture was diluted with DCM and washed with H₂O (2×) and a saturated solution of NaHCO₃ (2×). The organic layer was dried over Na₂SO₄, filtered and concentrated to dryness. The crude product was purified by gradient silica gel flash chromatography (DCM: 99:1 to 98:2 v/v) affording 1-(3',4'-dichloro-2-fluorobiphenyl-4-yl)cyclopropane carboxylic acid 2-acetylmethylamino-1-(acetylmethylamino methyl) ethyl ester (22.9 mg, 28.5% yield) as a colorless oil.

$^1$H NMR (300 MHz, DMSO-d6, 353K) ppm: 7.76 (dd, 1H), 7.71 (d, 1H), 7.54 (m, 1H), 7.51 (t, 1H), 7.21-7.33 (m, 2H), 5.24 (br, s, 1H), 3.40-3.67 (m, 2H), 3.33 (dd, 2H), 2.85 (br. s., 6H), 1.94 (br. s., 6H), 1.46-1.67 (m, 2H), 1.22-1.39 (m, 2H).

Example 6

Preparation of acetic acid 1-[(acetylmethylamino)methyl]-2-{[1-(3',4'-dichloro-2-fluorobiphenyl-4-yl)cyclopropanecarbonyl]-methylamino}ethyl ester (C5)

Scheme 7

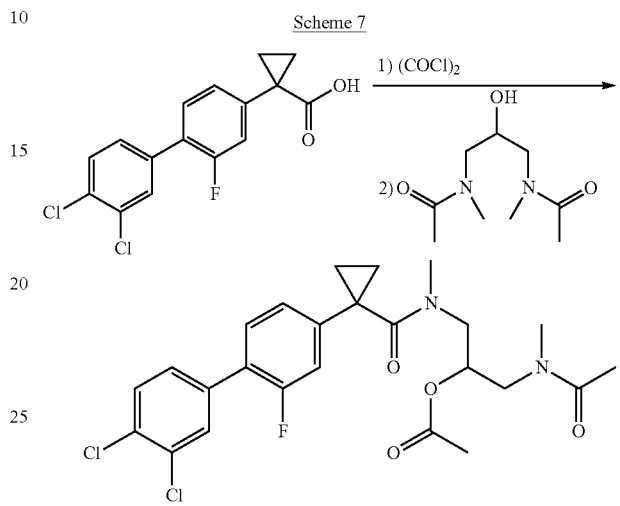

To a suspension of 1-(3',4'-dichloro-2-fluorobiphenyl-4-yl)cyclopropane carboxylic acid (1630 mg, 5.012 mmol) in DCM (55 mL) containing a few drops of DMF, under nitrogen atmosphere, at 0° C., oxalyl dichloride (0.849 mL, 10.02 mmol) was added dropwise, and the reaction was stirred at room temperature for 20 minutes. Solvent was evaporated, and the residue taken up with toluene and dried under vacuum, obtaining crude acyl chloride. Acyl chloride was dissolved in DCM (10 mL) and added dropwise, at 0° C., under nitrogen atmosphere, to a solution of N-[3-(acetylmethylamino)-2-hydroxypropyl]-N-methylacetamide (I5) (676 mg, 3.342 mmol) and triethylamine (2.8 mL, 20.08 mmol) in DCM (50 mL). The reaction was stirred at r.t. overnight and then heated at 40° C. for 2 hours. The reaction mixture was diluted with DCM and washed with H₂O (2×) and a saturated solution of NaHCO₃ (2×). The organic layer was dried with Na₂SO₄, filtered and concentrated to dryness. The crude thus obtained was purified by silica gel flash chromatography (DCM:methanol 99:1 v/v) affording acetic acid 1-[(acetylmethylamino)methyl]-2-{[1-(3',4'-dichloro-2-fluorobiphenyl-4-yl)cyclopropanecarbonyl]methylamino}ethyl ester (350 mg, 21% yield) as pale yellow foam.

$^1$H NMR (300 MHz, DMSO-d6, 353K) ppm: 7.75 (dd, 1H), 7.70 (d, 1H), 7.53 (dd, 1H), 7.51 (t, 1H), 7.11 (dd, 1H), 7.06 (dd, 1H), 5.12-5.45 (m, 1H), 3.31-3.69 (m, 4H), 2.97 (s, 3H), 2.91 (s, 3H), 1.97 (s, 3H), 1.96 (s, 3H), 1.32-1.47 (m, 2H), 1.23-1.32 (m, 2H).

LC-MS (ESI POS): 509.06 (MH+).

Note that although the procedure is similar to that utilized to synthesize C4 (second method, see Example 5), with the exception that also DMAP was added in the coupling step of Example 5 but not of Example 6, the isolated product is different, being acetic acid 1-[(acetylmethylamino)methyl]-2-{[1-(3',4'-dichloro-2-fluorobiphenyl-4-yl)cyclopropanecarbonyl]methylamino}ethyl ester in Example 6 and 1-(3', 4'-dichloro-2-fluorobiphenyl-4-yl)cyclopropane carboxylic acid 2-acetylmethylamino-1-(acetylmethylaminomethyl) ethyl ester in Example 5.

Biological Characterization

Example 7

Brain Penetration of Parent Compound (CHF 5074) after Pro-Drug Administration

Pro-drugs were administered to the rat by oral gavage at 62 µmol/kg equimolar dose to the administration of CHF 5074 to assess the brain penetration of the active moiety. Only CHF 5074 was quantified in plasma, brain, and cerebrospinal fluid (CSF). Sprague-Dawley male rats (body weights 150-175 g at the time of the supply) were used for brain and CSF penetration study in the rat. The animals were originally supplied by Harlan Lab., Udine. All animals were weighed on the day of each treatment. Clinical signs were monitored at regular intervals throughout the study in order to assess any reaction to treatment. Each animal was uniquely identified with a number before the experiment. Nine animals were treated by oral gavage of the test pro-drug at the target dose of 62 µmol/kg/5 mL of formulate (0.2 M phosphate buffer pH 7.4 (50%)+PEG 400 (40%)+ethanol (10%)) and ten minutes before the scheduled time points, i.e. 16, 24, and 48 hours, rats were anaesthetized by chloral hydrate (300 mg/kg i.p.), and placed on a stereotaxical frame, where the cerebrospinal fluid was extracted by the *cisterna magna* (see Hudson LC, *Laboratory Animal Sci.*, 44, 358, 1994, which is incorporated herein by reference). CSF samples (about 50-80 µL) were collected in labeled eppendorf, placed on ice, and frozen at −80° C. Blood and brain were collected after the sacrifice of the animals.

Blood samples were collected in heparinized eppendorfs (Heparin Vister 5000 U.I./mL, Marvecs Pharma), plasma prepared and collected to uniquely labeled eppendorfs, and immediately frozen at −80° C. Plasma calibration curves were prepared by adding 90 µL of plasma, spiked with 10 µL of the working standard (WS) solutions, into a Sirocco protein precipitation plate containing 300 µL of methanol spiked with 10 µL of an internal standard (I.S). The plate was shaken for 15 minutes and then filtered under vacuum (15 mm Hg) for about 5 minutes. Filtered solutions were placed in the autosampler at 15° C. Quality control (QC) plasma samples were prepared in an analogous way from QC stock solutions.

Brains were weighed and homogenized in ammonium formate 10 mM at 0.1 g/mL. 90 µL of blank brain homogenate were spiked with 104 of WS solutions of CHF 5074 and were added into a Sirocco protein precipitation plate containing 3004 of methanol spiked with 104 of the I.S. The plate was shaken for 15 minutes, and then filtered under vacuum (15 mm Hg) for about 5 minutes. Filtered solutions were placed in the autosampler at 15° C. Calibration curve for CFS samples was similarly prepared using artificial CSF. Brain samples and CSF samples were prepared by adding 100 µL into a Sirocco protein precipitation plate containing 300 µL of methanol spiked with 10 µL of the I.S. Samples were analyzed on an API 2000 Applied Biosystems Mass spectrometer (Interface APCI negative, CAD 3, T 500C, GS1 80, GS2 20) equipped with a UPLC Waters with an autosampler provided with the integrated software Analyst 1.4.2. The lower limit of quantification (LLOQ) was set up at 10 ng/mL for CHF5074. Chromatograms were integrated by the software on the Q1/Q3 transitions of the compound and of the I.S. The area of the samples was automatically interpolated on the calibration curves of the correspondent sample list. The results as mean of three determinations are reported in Table 1. For the concentrations in plasma and brain, S.D. is also given.

For all the compounds, the brain penetration of CHF 5074 was calculated as $AUC_{brain}/AUC_{plasma}$ ratio×100.

TABLE

Concentrations, AUC (0-48 hrs) in plasma and brain and brain/CSF penetration of free CHF 5074 after administration of its pro-drugs vs CHF5074 per se.

| Compound | Conc. at 48 hrs (ng/ml) | | AUC 0-48 hrs (ng/ml*h) | | AUC ratio*100 brain/plasma |
|---|---|---|---|---|---|
| | plasma | brain | plasma | brain | |
| C1 | 70233 ± 10917 | 4252 ± 606 | 1991436 | 114564 | 5.8 |
| C3 | 68617 ± 10809 | 4043 ± 894 | 1897004 | 112716 | 5.9 |
| C4 | 9282 ± 603 | 1146 ± 378 | 840964 | 63069 | 7.5 |
| C5 | 5390 ± 1063 | 373 ± 74 | 331752 | 17731 | 5.3 |
| CHF 5074 | 15288 ± 4510 | 577 ± 158 | 1549856 | 71704 | 4.6 |

The results show, that, after oral administration of the pro-drugs of the present invention significant higher brain penetration of the drug is obtained in comparison to CHF 5074 given per se, indicating that said pro-drugs are capable of releasing in situ the active moiety.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

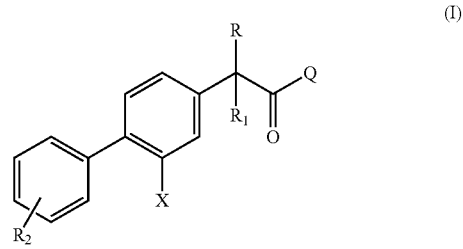

wherein:

X is a halogen selected from the group consisting of F, Cl, Br, and I;

R and $R_1$ are the same and are $(C_1-C_4)$-alkyl or, together with the carbon atom to which they are bonded, form a 3 to 6 carbon atom saturated ring;

$R_2$ represents one or more halogen atoms;

Q is a group $Q_1$ or $Q_2$:

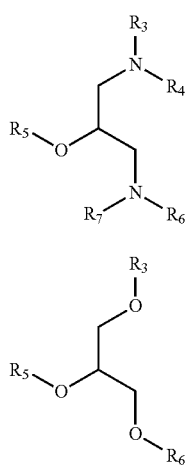

wherein:
$R_3$, $R_5$ and $R_6$ are each independently $(C_1$-$C_4)$-alkyl, $(C_2$-$C_{16})$-alkanoyl, or a bond connecting the group $Q_1$ or $Q_2$ to the rest of the molecule, with the condition that one and only one of $R_3$, $R_5$ and $R_6$ is a bond;
$R_4$ and $R_7$ are each independently H, $(C_1$-$C_4)$-alkyl, and $(C_2$-$C_{16})$-alkanoyl.

2. A compound according to claim 1, wherein X is fluorine and each $R_2$ is chlorine.

3. A compound according to claim 2, wherein R and $R_1$, together with the carbon atom to which they are bonded, form a 3 carbon atom ring.

4. A compound according to claim 2, wherein R and $R_1$ are both methyl.

5. A compound according to claim 1, having formula (Ia):

(Ia)

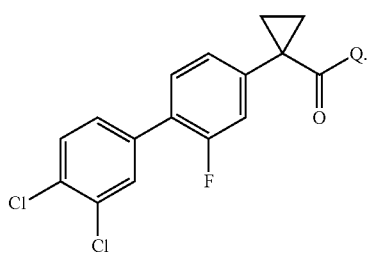

6. A compound according to claim 5, having formula (Ib):

(Ib)

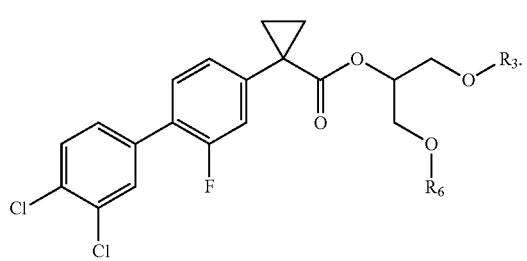

7. A compound according to claim 6, wherein $R_3$ and $R_6$ are the same or different from each other, and are independently selected from $(C_2$-$C_4)$-alkanoyl and $(C_{12}$-$C_{16})$-alkanoyl.

8. A compound according to claim 6, wherein $R_3$ and $R_6$ are the same or different from each other, and are independently selected from acetyl and hexadecanoyl.

9. A compound according to claim 5, having formula (Ic):

(Ic)

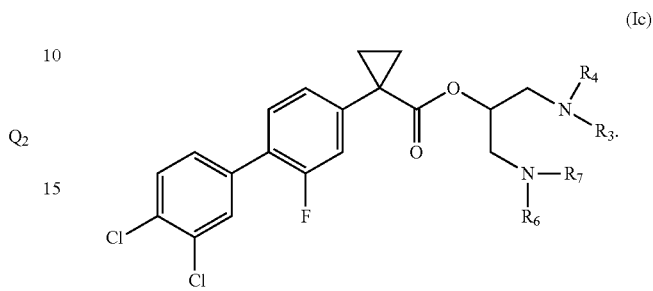

10. A compound according to claim 9, wherein $R_3$ and $R_6$ are the same or different from each other, and are independently selected from $(C_2$-$C_4)$-alkanoyl, and $R_4$ and $R_7$ are the same or different from each other, and are independently H or $(C_1$-$C_4)$-alkyl.

11. A compound according to claim 9, wherein $R_3$ and $R_6$ are both acetyl, and $R_4$ and $R_7$ are the same or different from each other, and are independently H or methyl.

12. A compound according to claim 5 having formula (Id):

(Id)

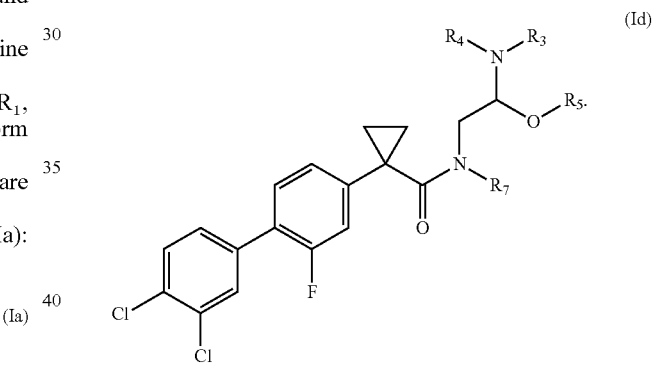

13. A compound according to claim 12, wherein $R_3$ and $R_5$ are the same or different from each other, and are independently selected from $(C_2$-$C_4)$-alkanoyl, and $R_4$ and $R_7$ are the same or different from each other, and are independently H or $(C_1$-$C_4)$-alkyl.

14. A compound according to claim 12, wherein $R_3$ and $R_5$ are both acetyl, and $R_4$ and $R_7$ are the same or different from each other, and are independently H or methyl.

15. A pharmaceutical composition, comprising a compound of formula (I) according to claim 1, optionally in combination with one or more pharmaceutically acceptable carriers and/or excipients.

16. A method for treating a neurodegenerative disease, comprising administering an effective amount of a compound according to claim 1 to a subject in need thereof.

17. A method according to claim 16, wherein said disease is Alzheimer's disease.

18. A method for improving cognitive function or treating cognitive function impairment, comprising administering an effective amount of a compound according to claim 1 to a subject in need thereof.

19. A method according to claim 17, wherein said impairment of cognitive function is caused by, or attributed to, mild cognitive impairment (MCI).

* * * * *